US00PP20558P2

(12) United States Plant Patent
Hanes

(10) Patent No.: US PP20,558 P2
(45) Date of Patent: Dec. 15, 2009

(54) ***PELARGONIUM* PLANT NAMED 'CANTE HOCORA'**

(50) Latin Name: ***Pelargonium L'Herit. ex Aiton* hybrid**
Varietal Denomination: Cante Hocora

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,126

(22) Filed: Nov. 6, 2008

(51) Int. Cl.
*A01H 5/00* (2006.01)

(52) U.S. Cl. ..... Plt./330

(58) Field of Classification Search ..... Plt./330
See application file for complete search history.

*Primary Examiner*—Annette H Para
(74) *Attorney, Agent, or Firm*—S. Matthew Edwards

(57) ABSTRACT

A new *Pelargonium* plant named 'Cante Hocora', particularly distinguished by the intense rose-red flower color, numerous relatively small inflorescences, dark-green foliage, small leaves without zonation, medium to strong vigor, and lowly mounding, horizontally spreading plant habit.

1 Drawing Sheet

Latin name of the genus and species of the plant claimed: *Pelargonium L'Herit. ex Aiton* hybrid.

Varietal denomination: 'Cante Hocora'.

BACKGROUND OF THE NEW PLANT

The present invention comprises a new *Pelargonium,* botanically known as *Pelargonium* hybrid (*Pelargonium*× *hortorum*×*Pelargonium tongaense*) and hereinafter referred to by the variety name 'Cante Hocora'.

'Cante Hocora' is a product of a planned breeding program. The new cultivar has rose-red, single-type flowers, dark green foliage, medium to strong vigor, and relatively compact structure.

'Cante Hocora' originated from a hybridization, respective self-pollination, made in February 2003 in a controlled breeding program in Gilroy, Calif. The seed and pollen parent was an unpatented inter-specific hybrid seedling identified as '9622-2'. '9622-2' has dark-red, single-type flowers, dark green foliage color, and a compact plant habit.

The resulting seeds were sown in May 2003. 'Cante Hocora' was selected as one flowering plant within the progeny of the stated cross in July 2003 in a controlled environment in Gilroy, Calif.

The first act of asexual reproduction of 'Cante Hocora' was accomplished when vegetative cuttings were taken from the initial selection in the fall of 2003 in a controlled environment in Gilroy, Calif.

Horticultural examination of plants grown from cuttings of the plant initiated in the spring of 2006 in Gilroy, Calif., and continuing thereafter, has demonstrated that the combination of characteristics as herein disclosed for 'Cante Hocora' are firmly fixed and are retained through successive generations of asexual reproduction.

'Cante Hocora' has not been observed under all possible environmental conditions. The phenotype may vary significantly with variations in environment such as temperature, light intensity and day length.

A Plant Breeder's Right for this cultivar was applied for in Canada on Dec. 24, 2007. 'Cante Hocora' has not been made publicly available more than one year prior to the filing of this application.

DESCRIPTION OF THE DRAWINGS

The accompanying photographic drawing shows typical flower and foliage characteristics of 'Cante Hocora' with colors being as true as possible with an illustration of this type. The photographic drawing shows a container of three flowering potted plants of the new variety and a close-up of the flowers. The whole plant photograph was taken in July 2008 and the close-up was taken in the June 2008 both in Gilroy, Calif. Both were grown in Gilroy, Calif. and were approximately 3–4 months old.

DETAILED BOTANICAL DESCRIPTION

The measurements were taken in Hillscheid, Germany, in late August/early September on plants that were growing, 3 each, in 45 cm diameter tubs outdoors in the trial field. Culture of these plants started in early March 2008 when rooted cuttings were potted into 12 cm containers and grown on benches in a greenhouse. They were transplanted in mid May and then placed outdoors.

Color Chart used: Royal Horticultural Society Colour Chart (R.H.S.) 2001

BRIEF SUMMARY OF INVENTION

The following observations, measurements, and comparisons describe plants grown outside in Hillscheid, Germany. The following traits have been repeatedly observed and are determined to be basic characteristics of the new variety. The combination of these characteristics distinguishes this *Pelargonium* as a new and distinct variety.

1. Single-type flowers of intense rose-red color
2. Numerous relatively small inflorescences, at short distance over the foliage canopy
3. Dark green foliage, relatively small leaves without zonation
4. Fairly compact plant habit, but medium to tall in size
5. Well-branched, mounding and horizontally spreading plant habit
6. Mid season spring flowering response
7. Suitable as a bedding plant, as ground cover and for larger containers

TABLE 1

DIFFERENCES BETWEEN THE NEW VARIETY 'CANTE HOCORA' AND A SIMILAR VARIETY

| | 'Cante Hocora' | 'Cante Coras' (U.S. Plant Pat. No. 15,653) |
|---|---|---|
| Flower color | RHS 58A-58B | Near RHS 52A |
| Foliage color | Dark green RHS 137A to 139A | Medium green |
| Plant habit | Tight | More open |
| Peduncles color and length | Brown with anthocyanin, and relatively short | Green, longer, so that inflorescences are higher above the foliage |

Plant:

*Form, growth and habit.*—Low, mounded a bit cushion-like, tight plant habit

*Plant height.*—28–30 cm.

*Plant height* (*inflorescence included*).—35–38 cm.

*Plant width.*—40–45 cm.

*Number of inflorescences per plant.*—About 25–35.

Stem:

*Color of stem.*—Mainly green, RHS 138A, in parts with anthocyanin, brown, RHS 200B.

*Length of stem.*—15–25 cm.

*Diameter.*—0.6–0.9 cm at mid portion.

*Length of internodes.*—1.0–2.5 cm.

*Texture.*—Covered with dense, short pubescence.

Foliage:

*Immature, leaf color, upper surface.*—Dark green, RHS 139A.

*Lower surface.*—RHS 137C.

*Mature, leaf color, upper surface.*—Dark green, near RHS 139A or between RHS 139A and 137A.

*Lower surface.*—RHS 138A.

*Length.*—3.5–4.0 cm.

*Width.*—6.3–7.0 cm.

*Leaf shape.*—Kidney-shaped to nearly semi-circular.

*Base shape.*—Cordate, with white open base.

*Apex shape.*—Rounded.

*Margin.*—Bi-crenate.

*Texture.*—Very short hair, hirtellous.

*Color of zone.*—Absent.

*Color of veins, upper surface.*—Indistinct, RHS 144A.

*Color of veins, lower surface.*—RHS 144B.

*Petiole color.*—RHS 143C.

*Petiole length.*—Approximately 7–12 cm.

*Diameter of petiole.*—2–2.5 mm.

*Texture.*—Rough with hair, hirtellous.

Inflorescence:

*Type.*—An umbel, incomplete umbrella shape.

*Start of flowering* (*50% of plants with open flowers*).—On May 5 (9 weeks old).

*Duration of flowering.*—Continuous flowering throughout the summer months.

*Number of inflorescences per plant.*—30–35.

*Number of flowers per inflorescence.*—8–12.

*Umbel diameter.*—7–8 cm mostly.

*Umbel depth.*—Approximately 3–5 cm.

*Color of peduncle.*—Basal color green, RHS 143B, upper part infused with anthocyanin, the resulting brown color increases to as deep a hue as RHS 187A.

*Length of peduncle.*—8–12 cm mostly, 16 cm maximum.

*Peduncle diameter.*—Relatively thin, 2–2.5 mm.

*Texture.*—Rough with relatively long hairs.

*Color of pedicel.*—Mostly dark purple, RHS 187A.

*Length of pedicel.*—3.3–3.8 cm.

*Diameter of pedicel.*—1 mm.

*Texture.*—Covered with dense short hair and and with sparse longer hairs.

Corolla:

*Form.*—Single-type, zygomorphic, the petals are not overlapping.

*Diameter/length of flower.*—4.5–4.8 cm.

*Vertical diameter/depth of flower.*—1.0–1.5 cm.

*Number of petals.*—5.

*Color upper petals, upper surface.*—RHS 58A to 58B, at base RHS 52A, weak veins at base, color near RHS 60A.

*Color upper petals, lower surface.*—A little more bluish than RHS 52A.

*Length of upper petals.*—2.7–2.8 cm.

*Width of upper petals.*—1.5–1.6 cm.

*Color lower petals, upper surface.*—RHS 58B to 58C.

*Color lower petals, lower surface.*—Between RHS 52A and 52B.

*Length of lower petals.*—2.5–2.7 cm.

*Width of lower petals.*—1.6–1.8 cm.

*Petal shape.*—Spatulate to obovate.

*Apex shape.*—Rounded.

*Margin.*—Mainly entire, slightly crenulated at the tip of upper petals.

*Petal texture.*—Smooth.

*Number of petaloids* (*if any*).—None.

Bud (just before opening):

*Color.*—RHS 43A to 50A.

*Length.*—1.6–1.9 cm.

*Width.*—0.6 cm.

*Shape.*—Narrow, spindle-shape to elliptic.

Calyx:

*Number of sepals.*—5.

*Color of sepals.*—Mainly deep brown, RHS 183A.

*Length of sepals.*—8–10 mm.

*Width of sepals.*—4 mm for the largest sepal, 2–3 mm for the other ones.

*Sepal shape.*—Lanceolate.

*Apex shape.*—Acute, a little pointed.

*Margins.*—Entire.

*Texture.*—Covered with thin, relatively long hair.

Reproductive organs:

*Pistil.*—One.

*Length.*—8–9 mm.

*Style color.*—Pink, RHS 63B to 63C.

*Style length.*—4 mm.

*Stigma color.*—RHS 63B.

*Number of stamen.*—7.

*Length of anthers.*—2–3 mm.

*Anther color.*—RHS 61 C.

*Length filaments.*—6–7 mm.

*Color of filaments.*—White (at base) to pink, RHS 63B.

*Pollen amount.*—Moderate (typical for the species).

*Color of pollen.*—Orange-yellow, RHS 25A.

*Fertility/seed set.*—A little seed set observed in late summer and early fall.

Disease/pest resistance: Disease resistance or susceptibility has not been observed on this hybrid.

What is claimed is:

1. A new and distinct variety of *Pelargonium* plant named 'Cante Hocora', substantially as illustrated and described herein.

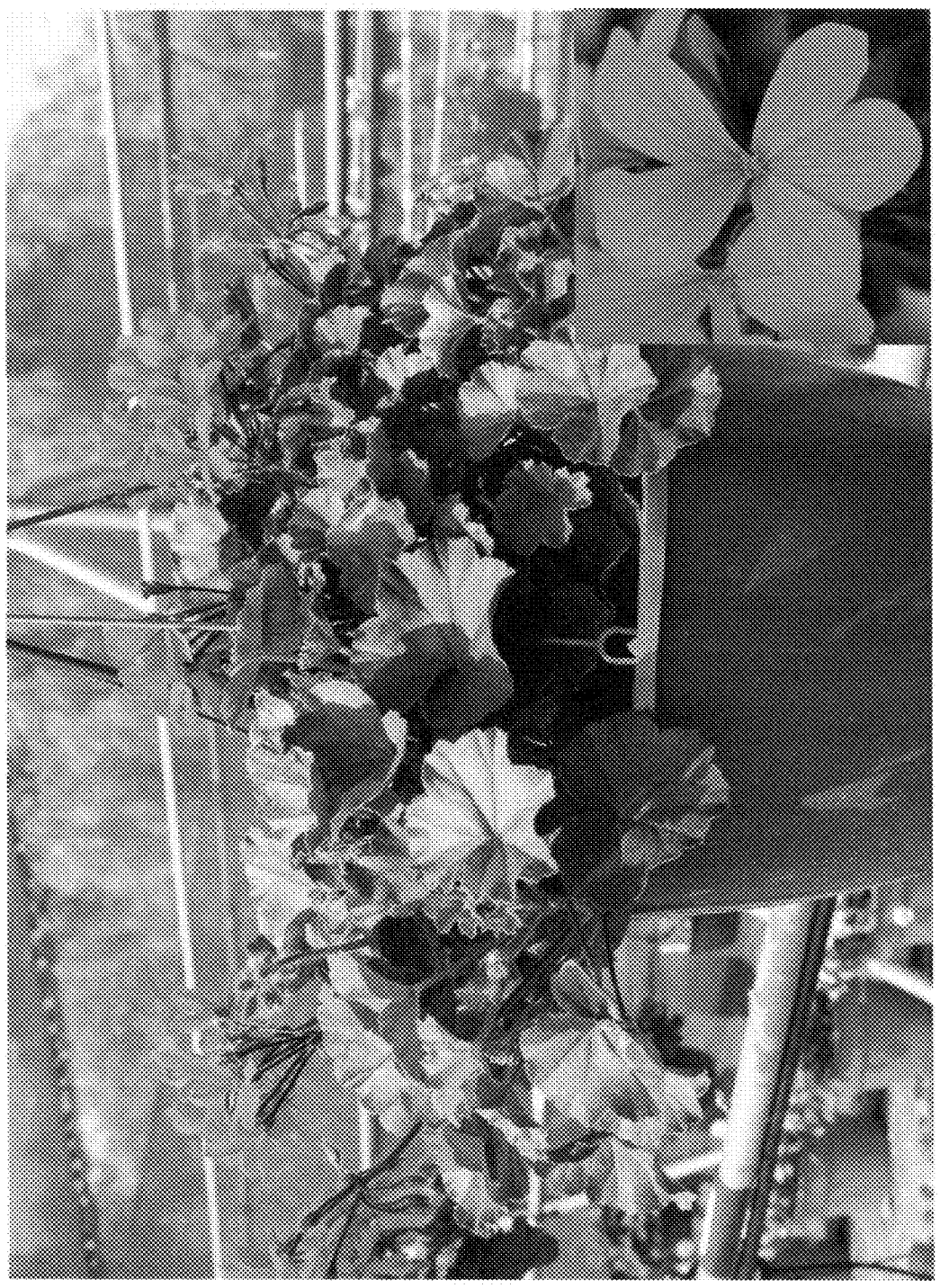

* * * * *